United States Patent
Setoyama et al.

(10) Patent No.: US 7,608,746 B2
(45) Date of Patent: Oct. 27, 2009

(54) PROCESS FOR PRODUCING PROPYLENE

(75) Inventors: Tohru Setoyama, Yokohama (JP); Yumiko Yoshikawa, Yokohama (JP); Kagoto Nakagawa, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 181 days.

(21) Appl. No.: 11/450,331

(22) Filed: Jun. 12, 2006

(65) Prior Publication Data

US 2006/0229482 A1    Oct. 12, 2006

Related U.S. Application Data

(63) Continuation of application No. PCT/JP2004/018555, filed on Dec. 13, 2004.

(30) Foreign Application Priority Data

| Dec. 12, 2003 | (JP) | 2003-415367 |
| Feb. 23, 2004 | (JP) | 2004-045917 |
| Feb. 23, 2004 | (JP) | 2004-045918 |
| Feb. 23, 2004 | (JP) | 2004-045919 |
| Mar. 30, 2004 | (JP) | 2004-101075 |
| Apr. 28, 2004 | (JP) | 2004-134145 |
| May 24, 2004 | (JP) | 2004-153547 |

(51) Int. Cl.
*C07C 1/00* (2006.01)

(52) U.S. Cl. ........................ 585/640; 585/639
(58) Field of Classification Search ................. 585/639, 585/640
See application file for complete search history.

(56) References Cited

U.S. PATENT DOCUMENTS

| 4,386,230 A | 5/1983 | Hogan et al. |
| 6,740,790 B2 | 5/2004 | Kuechler et al. |
| 7,015,369 B2 | 3/2006 | Hack et al. |
| 2002/0169349 A1 | 11/2002 | Kuechler et al. |
| 2003/0139635 A1 | 7/2003 | Hack et al. |

FOREIGN PATENT DOCUMENTS

| EP | 0 054 387 A1 | 6/1982 |
| EP | 0 060 103 A1 | 9/1982 |
| EP | 0 882 692 A1 | 12/1998 |
| JP | 57-128637 | 8/1982 |
| JP | 59-222429 | 12/1984 |
| JP | 4-217928 | 8/1992 |
| JP | 5-65488 | 3/1993 |
| JP | 2003-511484 | 3/2003 |
| JP | 2003-535069 | 11/2003 |
| WO | WO 01/23500 A1 | 4/2001 |
| WO | WO 01/92190 A1 | 12/2001 |

OTHER PUBLICATIONS

Xianchun et al, Applied Catalysis A: General, 2001, vol. 218, No. 1-2, pp. 241-250 (figs. 3, 5).
Graham et al., Catalysis Today, 1990, vol. 6, No. 3, pp. 279-306.

*Primary Examiner*—In Suk Bullock
(74) *Attorney, Agent, or Firm*—Oblon, Spivak, McClelland, Maier & Neustadt, L.L.P.

(57) ABSTRACT

Propylene is prepared by a process for producing propylene, comprising: contacting a reaction mixture of ethylene and methanol and/or dimethyl ether in the presence of a catalyst while controlling the amount of ethylene that is discharged from the reaction system to a reduced level in comparison to the amount of ethylene that is being fed into the reaction system, and while controlling the yield of propylene to at least 40 mol %, based on the sum of the number of moles of methanol and two times the number of moles of dimethyl ether, which are being fed into the reaction system.

19 Claims, No Drawings

PROCESS FOR PRODUCING PROPYLENE

FIELD OF THE INVENTION

The present invention relates to a process for producing propylene from ethylene and methanol and/or dimethyl ether.

DESCRIPTION OF THE BACKGROUND

With respect to processes for the production of paraffins, olefins and aromatic hydrocarbons, various techniques have been investigated which include not only processes of cracking petroleum, but also processes which use, as raw materials, methanol and dimethyl ether obtained from a hydrogen/CO mixed gas that in turn is obtainable by modifying natural gas by using a new energy source. Especially, in more recent processes that have been developed, in comparison to older known processes, the products obtained contain substantially no sulfur compounds and are thus expected to be environmentally-friendly petrochemical raw materials.

Such processes for producing paraffins, olefins and aromatic hydrocarbons by using methanol and dimethyl ether as raw materials, are usually named, depending upon the types of the main products produced. That is, a process in which gasoline is obtained as the main product is referred to as the MTG process, and a process by which lower olefins, as the main products, is referred to as the MTO process. A process of producing propylene, in particular, of the lower olefins, as the main component, is referred to as the MTP process.

However, in a case where propylene is obtained from methanol (see e.g. Patent Documents 1 to 3), theoretically, one molecule of propylene will be formed from three molecules of methanol. However, the yield of propylene product, based on the molar amount of the raw material methanol, is only 33% at maximum. Moreover, the weight of water that is formed as a by-product is substantial. Accordingly, such a process can not be regarded as a preferred industrial process from the viewpoint of e.g. the efficiency of installation costs.

On the other hand, with regard to the MTP process, it is also known that propylene is obtained from ethylene and methanol (non-Patent Document 1). However, in this process, the yield of propylene based on the amount of raw material methanol does not exceed 40 mol % and is thus inadequate.

Patent Document 1: JP-A-59-222429
Patent Document 2: JP-A-4-217928
Patent Document 3: US-A-2003-139635
Non-Patent Document 1: Applied Catalysis A: General 218 (2001), 241-250 In the prior art known processes, the yield of propylene, based on the number of moles of the raw material methanol, is low and accordingly, such process embodiments are inadequate as industrial production processes.

SUMMARY OF THE INVENTION

One object of the present invention is to provide a process for producing propylene in a yield higher than obtained in conventional processes in the case where propylene is produced from ethylene and methanol.

Accordingly, these and other objects of the present invention as hereinafter will become more readily apparent can be attained in a method of obtaining propylene in high yield when ethylene is reacted with methanol and/or dimethyl ether by contacting a reaction mixture of ethylene and methanol and/or dimethyl ether in the presence of a catalyst while controlling the amount of ethylene that is discharged from the reaction system to a reduced level in comparison to the amount of ethylene that is being fed into the reaction system, and while controlling the yield of propylene to at least 40 mol %, based on the sum of the number of moles of methanol and two times the number of moles of dimethyl ether, which are being fed into the reaction system.

DETAILED DESCRIPTION OF THE PREFERRED EMBODIMENTS

In the process of the present invention, in order to increase the yield of propylene from ethylene, the reaction pressure is preferably adjusted within a range of at least 0.1 kPa to less than 2 MPa, and the amount of ethylene fed into the reaction system is adjusted within a mole ratio range of at least 1 to at most 20, based on the sum of the number of moles of methanol and two times the number of moles of dimethyl ether, which are fed into the reaction system. Further, it is preferred that the weight hourly space velocity per unit weight of a catalytically active component, of the sum of methanol and dimethyl ether calculated as methanol, which are fed into the reaction system, is adjusted within a range of at least 0.01 $hr^{-1}$ to at most 70 $hr^{-1}$.

(1) Reaction Substrate (Raw Material)

The process of the present invention is a gas phase reaction, and the raw material of the present reaction is composed of a mixed gas comprising ethylene and methanol and/or dimethyl ether. This mixed gas may optionally contain, in addition to ethylene and methanol and/or dimethyl ether in a gaseous state, a gas that is inert to the reaction, such as helium, argon, nitrogen, carbon monoxide, carbon dioxide, hydrogen, water, a paraffin, a hydrocarbon such as methane, an aromatic compound or a mixture thereof, for example, in an amount of from 1 mol % to 99 mol % as the concentration in the mixed gas. Of these gaseous materials, water vapor, i.e. steam, is preferred.

Further, the mixed gas is not particularly limited with respect to the form in which it is fed into the reactor as long as it is mixed at the time of the reaction. Ethylene and methanol and/or dimethyl ether, and, if necessary, other gases that are inert to the reaction, may, respectively, be fed into the reactor, or they may be mixed into the gas mixture prior to being fed into the reactor.

(1)-a Ethylene

The ethylene that is used in the present invention is not particularly limited, and can be obtained by various known methods. Two such methods are the catalytic cracking or steam cracking of a petroleum-base material. Another method is one in which a FT (Fischer-Tropsch) reaction is conducted using as a raw material a hydrogen/CO mixed gas obtainable by gasification of coal. Still another method is the dehydrogenation or oxidative dehydrogenation of ethane. Yet another method of ethylene production is a metathesis reaction and a homologation reaction of propylene. Ethylene can also be produced from an oxygenated material such as methanol and/or dimethyl ether by a catalytic reaction with a solid acid catalyst. Another method of ethylene production is by dehydration of the corresponding alcohol (ethanol). It is also possible to use an ethylene material that contains other gaseous materials that are present as a result of the particular process that is used, or purified ethylene may be used.

Of the various methods by which ethylene is produced, the catalytic cracking or steam cracking of a petroleum-base material, is preferred. A more preferred method of producing ethylene is by catalytic cracking or steam cracking of a hydrocarbon raw material that has at least two carbon atoms and a boiling point of up to 300° C. and that has a sulfur content that is reduced by desulfurization, such as ethane, propane, a butane/butylene mixture, naphtha, light NGL, heavy NGL or kerosene light oil in a catalytic or steam cracking furnace that has an outlet temperature ranging from 760 to 900° C.

It is preferred to employ, as the ethylene starting material, ethylene that is obtained by an olefin production facility by thermal decomposition of naphtha, whereby in the olefin production facility, the yield balance of ethylene and propylene can be changed to substantially increase the propylene/ethylene ratio.

Further, it is preferred to use ethylene that is obtained from a lower content olefin production facility utilizing methanol and/or dimethyl ether as a starting material, whereby in the lower olefin production facility, the yield balance of ethylene and propylene can be changed to substantially increase the propylene/ethylene ratio.

Still further, it is preferred to use ethylene that is obtained from an ethylene production facility by the steam cracking of ethane, whereby propylene can be produced using ethane separated mainly from natural gas, as the raw material.

It should be noted that olefins which are obtained by the thermal decomposition of naphtha, which is commonly used for producing olefins such as ethylene and propylene, usually contain about 28 wt % of ethylene, about 17 wt % of propylene and about 11 wt % of butene/butadiene on average, whereby there is a limiting extent to which the yield balance of ethylene and propylene can be changed depending upon the required balance of the two olefins. Various thermal decomposition methods have been studied in this respect, but in these methods, it is difficult to substantially change the yield balance. In the process for producing a lower olefin such as ethylene, propylene or butene from methanol and/or dimethyl ether, as disclosed in the above mentioned Patent Documents 3 and 4, Document 3, for example, describes a product of about 50 wt % propylene and about 20 wt % butene, based on about 10 wt % ethylene. Another process for selectively producing a lower olefin is known but it is still difficult to substantially change the yield balance of ethylene and propylene. Also in a process for producing ethylene by an ethylene production facility by steam cracking of ethane, although the composition of ethylene-containing products may differ depending upon the raw material composition, ethylene is mainly obtained, and it is difficult to obtain propylene.

Under these circumstances, the present invention provides a process which is useful for efficiently producing propylene from ethylene. Namely, the process for producing propylene of the present invention is an important technique which makes it possible to change the yield balance of ethylene and propylene in the above mentioned olefin production facility. Olefin production facilities (i), (ii) and (iii) will now be described.

(i) Facility for the Production of Olefins by Thermal Decomposition of Naphtha

A suitable steam cracking facility for the production of olefins by the thermal decomposition of naphtha in the present invention is now described. Steam cracking is commonly used to produce olefins such as ethylene, propylene, and the like. A typical steam cracking facility is a tubular heating furnace. One such method is the front end methane-removal process, in an embodiment of which naphtha is introduced into a thermal decomposition furnace together with steam and thermally decomposed at a temperature ranging from about 760 to 900° C., whereupon hydrocarbons obtained are quenched and then led to a fractionating column in which tar is produced at the bottom of the column, a gas oil is obtained from the side of the column and hydrocarbons are obtained from the top portion of the column. The hydrocarbons of the top fraction are quenched for separation into hydrocarbons having mainly at most 5 carbon atoms and a mixture of water derived from steam and hydrocarbons having mainly at least 6 carbon atoms. The mixture of water and hydrocarbons having mainly at least 6 carbon atoms is then separated. Further, the water that is separated is re-used via a steam generator as steam to be re-introduced into the thermal decomposition furnace. However, the separated water contains non-volatile hydrocarbons, and a part of the water will be disposed for removal of non-volatile hydrocarbons. Fresh water is supplied to supplement the supply of water.

Hydrocarbons having mainly at most 5 carbon atoms are obtained by quenching the top fraction from the column. The fraction is compressed in a compressor, and then, sulfur compounds are removed at an alkali-cleaning section. The decomposition material, after passing through a drying section, is passed to a methane-removing column, whereby methane and hydrogen are recovered as the top fraction. At the same time, the bottom fraction is discharged to an ethane-removing column, whereby acetylene in an ethane-ethylene mixture as the top fraction is converted in a hydrogenation reactor to ethane/ethylene which is passed to an ethylene fractionating column, and at the same time, the bottom fraction is passed to a propane-removing column. Methylacetylene and propadiene in the propane/propylene mixture, as the top fraction, are converted in a hydrogenation reactor to propane/propylene, which is sent to a propylene fractionating column, and at the same time, the bottom fraction is passed to a butane-removing column. In the ethylene fractionating column, ethylene product is recovered from the side of the column, and ethane, as the bottom fraction, is recycled to the decomposition furnace. In the propylene fractionating column, propylene product is recovered from the side of the column, and at the same time, propane, as the bottom fraction, is recycled to the decomposition furnace. In this manner, ethylene of high purity at a level of 99.95% and propylene of high purity at a level of 99.0% are separated and recovered.

Another embodiment of another method is a front end propane-removing process. The decomposition product after passing through the drying section as described above, is passed to a propane-removing column, whereby acetylene, methylacetylene and propadiene in the ethane/ethylene and propane/propylene mixtures of the top fraction are converted by a hydrogenation reactor to ethane/ethylene and propane/propylene, which are passed to a methane-removing column, and at the same time, the bottom fraction is passed to a butane removing column. In the methane removing column, methane and hydrogen are recovered as the top fraction, and at the same time, the bottom fraction is passed to an ethane-removing column, whereby ethane/ethylene as the top fraction of the ethane-removing column is sent to an ethylene fractionating column, and at the same time, the bottom fraction is passed to a propylene fractionating column. In the ethylene fractionating column, ethylene product is recovered from the side of the column, and at the same time, ethane as the bottom fraction is recycled to the decomposition furnace. Further, in the propylene fractionating column, propylene product is recovered from the side of the column, and at the same time, propane as the bottom fraction is recycled to the decomposition furnace.

Another variation of the above mentioned front end propane-removing process, involves passing the top fraction of the propane-removing column to an ethane-removing column, i.e. not to a methane-removing column. The top fraction of the propane-removing column comprises acetylene and methylacetylene, and in the case where methylacetylene is present in a large amount, it may be passed through the hydrogenation reactor in the same manner as mentioned above and then may be passed to the ethane-removing column. Further, in the case where the methylacetylene content of the gas mixture is small, it may be passed to the ethane-removing column without passing through the hydrogenation reactor, whereupon acetylene in methane, hydrogen and an ethane/ethylene mixture as the top fraction of the ethane-removing column may be passed through the hydrogenation reactor and converted to ethane/ethylene. The top fraction of the ethane-removing column may be passed through a hydrogen separator following the hydrogenation reaction, installed as the case requires, and then may be sent to the methane-removing column, and at the same time, the bottom fraction will be sent to a propylene fractionating column. In the methane-removing column, methane as the top fraction will be recovered, and at the same time, ethane/ethylene as the bottom fraction will be passed to an ethylene fractionating column. In the propylene fractionating column, propylene product is recovered from the side of the column, and at the same time, propane as the bottom fraction is recycled to the decomposition furnace. In the ethylene fractionating column, ethylene product is recovered from the side of the column, and at the same time, ethane as the bottom fraction is recycled to the decomposition furnace.

Further, in still another embodiment, a front end ethane-removing process is also available wherein the decomposition product, after passing through the drying section as mentioned above, is passed to an ethane-removing column.

In the present invention, propylene is preferably produced by reacting ethylene obtained from the above facility for the production of olefins by thermal decomposition of naphtha, with a gas containing methanol and/or dimethyl ether. The process uses water, formed as a by-product, as a steam-generating source in the thermal decomposition of naphtha. It is thereby possible to reduce the costs involved for the production of steam for the thermal decomposition of naphtha.

As mentioned above, the heat employed for the thermal decomposition of naphtha employs water as a diluting gas for naphtha. However, a portion of the water that is recovered must be disposed of and is not re-used in the reactor. Depending upon the operational conditions of the heat decomposition furnace, the amount of water may therefore be insufficient. On the other hand, at the time of producing propylene from ethylene and methanol and/or dimethyl ether, 1 mol of water is produced as a by-product per mole of methanol and/or dimethyl ether. This by-product water can then be used to supplement the water needed for generation of steam for the heat decomposition furnace.

It is possible to utilize, for example, a portion of the water formed as a by-product at the time of producing propylene, as a diluting agent for ethylene and a gas comprising methanol and/or dimethyl ether in the reaction for producing propylene and to adopt a method, e.g. of supplying the remaining water to the steam-generating apparatus for the thermal decomposition of naphtha. A portion of the water recovered from steam employed for the thermal decomposition of naphtha may be utilized as a diluting agent for ethylene and a gas comprising methanol and/or dimethyl ether in the reaction of ethylene with methanol and/or dimethyl ether.

Here, ethylene that is produced by a facility for the production of olefins by thermal decomposition of naphtha is meant to include not only ethylene obtained via an ethylene fractionating column in the above front end methane-removing process, front end propane-removing process and front end ethane-removing process, but also an ethane/ethylene mixture that is obtained after converting acetylene in an ethane/ethylene mixture as the top fraction of the ethane removing column in the above front end methane-removing process to ethane/ethylene by a hydrogenation reactor, an ethane/ethylene mixture as the top fraction of the ethane-removing column in the above front end propane removing process, the mixture containing ethylene after converting acetylene in the methane, hydrogen and ethane/ethylene mixture as the top fraction of the ethane-removing column in the above mentioned another variation of the front end propane-removing process to ethane/ethylene by a hydrogenation reactor as the case requires, and the mixture containing ethylene after converting acetylene included in the methane, hydrogen and ethane/ethylene mixture as the top fraction of the ethane-removing column in the above front end ethane-removing process to ethane/ethylene by a hydrogenation reactor. Further, the mixture containing ethylene in the above mentioned another variation of the front end propane-removing process and the above mentioned front end ethane-removing process may also be one that has at least a part of hydrogen and/or ethane present in such a mixture separated as the case requires.

Among the several methods mentioned, a preferred method is to employ an ethane/ethylene mixed gas that is obtained from the top fraction of the above ethane-removing column as the ethylene obtained by a facility for the production of olefins by thermal decomposition of naphtha. It is thereby possible to reduce the load in the ethylene fractionating column as compared with the case where ethylene product recovered from the side of the ethylene fractionating column is used as a raw material ethylene for reaction with methanol and/or dimethyl ether. At the same time, the ethane that is present in an amount ranging from about 10 to 20% in the ethane/ethylene mixed gas functions as a carrier in the reaction with methanol and/or dimethyl ether, whereby it is not necessary to supply a carrier substance from an outside source, and the reaction of the ethylene with methanol and/or dimethyl ether can be carried out very efficiently.

In this instance, the ethane/ethylene mixed gas that is obtained from the top fraction of the ethane-removing column is the mixed gas that is obtained after converting acetylene in the ethane/ethylene mixture as the top fraction in the above front end methane-removing process to ethane/ethylene by a hydrogenation reactor; or ethane/ethylene mixed gas that is obtained as the top fraction in the above front end propane-removing process; or the mixed gas obtained after converting acetylene in the methane, hydrogen and ethane/ethylene mixture as the top fraction in the above mentioned another variation in the front end propane-removing process, to ethane/ethylene by a hydrogenation reactor as the case requires; or a mixture obtained after converting acetylene included in the methane, hydrogen and ethane/ethylene mixture as the top fraction in the above front end ethane-removing process to ethane/ethylene by a hydrogenation reactor.

In the event the mixture containing ethylene in the above mentioned another variation of the front end propane-removing process and in the above mentioned front end ethane-removing process, at least a part of hydrogen and/or methane present in the mixture may be separated as the case requires. For example, in order to separate at least a part of methane after separation of hydrogen, a method may be mentioned wherein it is withdrawn from the side of the methane-removing column in such a process. Here, at the time of separating at least a portion of methane, by leaving a portion of methane, it is possible not only to reduce the load in the ethylene fractionating column as mentioned above but also to reduce the load in the methane-removing column. At the same time, not only ethane, but also methane, present in the ethane/ethylene mixed gas functions as a carrier in the reaction with methanol and/or dimethyl ether and thus helps to efficiently conduct the reaction of ethylene with methanol and/or dimethyl ether.

(ii) Process for the Production of Lower Olefins from Methanol and/or Dimethyl Ether A process for the production of lower olefins from methanol and/or dimethyl ether is a conventional process as described in Patent Documents 1 to 4 above, and it is, for example, a process of producing lower olefins such as ethylene, propylene, butylene, and the like, by reacting methanol and/or dimethyl ether at a temperature ranging from 200 to 600° C. under a pressure ranging from 10 to 600 kPa in the presence of a solid acid catalyst or the like, if necessary, in the presence of water. Here, the ratio of methanol and/or dimethyl ether to water is preferably 1:0 to 2. The solid acid catalyst is preferably a silicon-containing compound. The silicon-containing compound may, for example, be silicon dioxide, but more preferred is a crystalline aluminosilicate, a metallosilicate or a crystalline aluminum phosphate, particularly preferably a zeolite. Further, the temperature preferably ranges from 300 to 600° C., and the pressure preferably ranges from 20 kPa to 1 MPa. In an example, methanol and/or dimethyl ether is reacted under the above described conditions, and the reaction gas is cooled, partially condensed and separated into three phases by a separator. Then, a liquid phase comprising higher fatty acids and aromatic compounds is removed, and the remainder, being an aqueous phase and a gas phase, is washed with water in a washing column, and from its top, a gas mixture containing $C_2$-$C_4$ olefins is removed and separated into $C_2$, $C_3$ and $C_4$ by a known method, followed by purification to obtain ethylene product, propylene product and butylene product. On the other hand, from the bottom, an aqueous phase containing unreacted methanol and dimethyl ether as an unreacted and intermediate product, is removed, and from the aqueous phase, methanol and dimethyl ether are separated and recycled to the reactor, while water is removed.

An embodiment of the separation/purification system for the gas mixture containing $C_2$-$C_4$ olefins, for example, is the gas mixture that is passed through sequentially in the order of e.g. an ethylene/ethane-removing column, a methanol-removing column, a propylene/propane-removing column and a butylene/butane-removing column, and the ethylene/ethane mixture as the top fraction of the ethylene/ethane-removing column is, if necessary, subjected to such treatment that acetylene in the mixture is converted to ethylene/ethane by a hydrogenation reactor. Then, the mixture is sent to an ethylene fractionating column via a methanol-removing column, and at the same time, the bottom fraction is passed to a propylene/propane-removing column, and the propylene/propane mixture as the top fraction of the propylene/propane-removing column is, if necessary, subjected to such treatment that methylacetylene and propadiene in the mixture are converted to propylene/propane in a hydrogenation reactor. Then, the mixture is sent to a propylene fractionating column, and at the same time, the bottom fraction is passed to a butylene/butane-removing column. In the ethylene fractionating column, ethylene product is recovered from the top of the column, and ethane is separated from the bottom of the column. Further, in the propylene fractionating column, propylene product is recovered from the top of the column, and propane is separated from the bottom of the column. Here, the ethylene product that is obtained from the above mentioned facility for the production of lower olefins from methanol and/or dimethyl ether may, for example, be not only the ethylene product recovered from the top of the ethylene fractionating column by subjecting an ethylene/ethane mixture as the top fraction of the ethylene/ethane-removing column to such a treatment that acetylene in the mixture is converted to ethylene/ethane in a hydrogenation reactor, as the case requires and then sending the heated material to the ethylene fractionating column via a methanol-removing column, but also an ethylene/ethane mixture as the top fraction of the ethylene/ethane-removing column, or the ethylene/ethane mixture after converting acetylene in the mixture to ethylene/ethane by the hydrogenation reactor, as the case requires.

(iii) Facility for the Production of Ethylene by Steam Cracking of Ethane

The steam cracking of ethane is a reaction wherein a mixture of alkanes containing mainly ethane is dehydrogenated, for example, at a temperature ranging from 500 to 900° C. under at least atmospheric pressure, whereby mainly alkanes and some dienes or alkynes, are obtained. A suitable separation/purification system for the obtained reaction mixture, for example, firstly is a fraction heavier than $C_3$. This fraction is separated in a front end type ethane-removing column, and a hydrocarbon mixture is recovered from the top of the column. Then, acetylene in the mixture is removed and converted to ethylene/ethane by a hydrogenation reactor, as the case requires. Thereafter, the mixture is sent to an ethylene fractionating column via a methane-removing column, and ethylene is recovered from the top of the column. Ethylene hereby obtained by the facility for the production of ethylene by steam cracking of ethane to be used for the reaction of the present invention may be not only ethylene product recovered from the ethylene fractionating column, but also an ethylene/ethane/methane/hydrogen mixture as the top fraction of the methane-removing column, or a mixture after subjecting the column top mixture of the front end ethane-removing column to such treatment that acetylene in the mixture is converted to ethylene/ethane by a hydrogenation reactor as the case requires.

(1)-b Methanol and Dimethyl Ether

The sources of production of methanol and dimethyl ether as raw materials are not particularly limited and may, for example, be coal or natural gas. Or, the sources may be a mixed gas of hydrogen/CO derived as a by-product from the iron industry, or the source may be the product of the modification of alcohols derived from plants. Yet another source is the product obtained by a fermentation method, or the source is organic substances such as recycled plastics or urban wastes. Among these methods, preferred is the method of obtaining the methanol and dimethyl ether by the hydrogenation of a mixed gas of hydrogen/CO.

(2) Catalyst

The catalyst that is used in the present invention is not particularly limited so long as it is a solid one that has Bronsted acid sites. For example, a known catalyst may be used such as a solid acid catalyst of e.g. a clay mineral such as kaolin. Another type of catalyst is that of a carrier such as clay which supports an acid such as sulfuric acid or phosphoric acid. Still other types are an acid type ion exchange resin; an aluminum phosphate; a mesoporous silica alumina such as Al-MCM41; a zeolite; or a lamellar zeolite such as ITQ-2.

Suitable solid acid catalysts include catalysts that have a large surface area, and catalysts having many acid sites. The BET specific surface area of a preferred solid acid catalyst is usually at least 100 $m^2/g$, preferably at least 200 $m^2/g$, more preferably at least 300 $m^2/g$ and usually at most 1,000 $m^2/g$, preferably at most 800 $m^2/g$, more preferably at most 700 $m^2/g$. Further, the pore volume is usually at least 0.01 cc/g, preferably at least 0.05 cc/g, more preferably at least 0.1 cc/g and usually at most 0.8 cc/g, preferably at most 0.6 cc/g, more preferably at most 0.5 cc/g. Among the solid acid catalysts, one which has an acid strength that is not so high is preferred. Suitable such examples include mesoporous silica, zeolite or lamellar zeolite.

(i) Zeolite

In the event the catalyst chosen is a zeolite, the structure of the zeolite may, for example, be those identified in terms of the codes of the International Zeolite Association (IZA), which are AEI, AET, AEL, AFI, AFO, AFS, AST, ATN, BEA, CAN, CHA, DDR, EMT, ERI, EUO, FAU, FER, LEV, LTL, MAZ, MEL, MFI, MOR, MTT, MTW, MWW, OFF, PAU, RHO, STT, TON, and the like. Preferred among these zeolites are those that have micropores having a pore diameter ranging from 3 to 9 Å.

Preferred zeolites include a porous crystalline silicate or a porous crystalline aluminophosphate, and a porous crystalline silicate modified with a metal element of Groups 1 to 14 of the Periodic Table other than silicon and aluminum elements, or a porous crystalline aluminophosphate similarly modified is more preferred.

(i)-a Porous Crystalline Silicate

Suitable porous crystalline silicates include a porous crystalline silicate, aluminosilicate, aluminophosphosilicate, borosilicate, aluminoborosilicate having a portion of the silicon substituted by aluminum and/or phosphorus and/or a boron, or a metal silicate having a portion of the silicon substituted by another element. Preferred silicates include a silicate, an aluminosilicate, an aluminophosphosilicate, a crystalline aluminosilicate substituted by an aluminoborosilicate, or the after-mentioned modified porous crystalline silicate. Further, the aluminosilicate is preferably one that has a molar ratio of $SiO_2/Al_2O_3$ of greater than 10.

The structures of such porous crystalline silicates may include those identified in terms of the codes of the International Zeolite Association (IZA) which are AEI, AET, AEl, AFI, AFO, AFS, AST, ATN, BEA, CAN, CHA, DDR, EMT, ERI, EUO, FAU, FER, LEV, LTL, MAZ, MEL, MFI, MOR, MTT, MTW, MWW, OFF, PAU, RHO, STT, TON, and the like. Of these types, AFI, BEA, CAN, CHA, DDR, EMT, ERI, EUO, FAU, FER, LEV, LTL, MAZ, MEL, MFI, MOR, MTT, MTW, MWW, OFF, PAU, RHO, STT and TON are preferred. Specifically, SSZ-24, and the like having a AFI structure, β, and the like having a BEA structure, Cancrinite, and the like having a CAN structure, Chabazite, SSZ-13, and the like having a CHA structure, sigma-1, and the like having a DDR structure, EMC-2, and the like having a EMT structure, Erionite, and the like having an ERI structure, EU-1, and the like having an EUO structure, USY, and the like having a FAU structure, Ferrierite, ZSM35, and the like having a FER structure, Levyne, and the like having a LEV structure, L-type zeolite, etc. having a LTL structure, Mazzite, and the like having a MAZ structure, ZSM5, and the like having a MFI structure, ZSM11, and the like having a MEL structure, Mordenite, and the like having a MOR structure, ZSM23, and the like having a MTT structure, ZSM12, and the like having a MTW structure, MCM22, and the like having a MWW structure, Offrrtite, and the like. having an OFF structure, ECR18, and the like having a PAU structure, Rho, and the like having a RHO structure, SSZ23, and the like having a STT structure, and ZSM22, and the like having a TON structure, may be mentioned. Among these materials, preferred are those having an AEI structure, a BEA structure, a CHA structure and a MFI structure, and particularly preferred are those having a BEA structure and a MFI structure. Specifically, β and ZSM5, for example, are mentioned.

The porous crystalline silicates may be various commercial products. Otherwise, porous crystalline silicates synthesized by known methods are disclosed, for example, in "Verified Syntheses Of Zeolitic Materials" ($2^{nd}$ Revised Edition 2001 Elsevier) published by IZA, may be employed.

Of the porous crystalline silicates mentioned above, a porous crystalline aluminosilicate containing aluminum may be one in which a portion of the aluminum atoms that constitute the porous crystalline silicate is subjected to removal by, e.g. steaming or acid treatment, so as to yield a crystalline aluminosilicate having a high silica/alumina ratio. A crystalline aluminosilicate that is particularly preferred is one that has a molar ratio of $SiO_2/Al_2O_3$ of at least 30, preferably at least 50, more preferably at least 100, and particularly preferably at least 200. On the other hand, as its upper limit, the $SiO_2/Al_2O_3$ molar ratio of the crystalline aluminosilicate is usually at most 1,000, more preferably at most 750, particularly preferably at most 500. With ZSM5, etc., the Al content can be adjusted not only by the above method but also by controlling the amount of aluminum at the time of zeolite synthesis.

A crystalline aluminosilicate is preferably one that has a BET specific surface area ranging from 200 m 2/g to 700 m²/g and a pore volume ranging from 0.1 cc/g to 0.5 cc/g.

(i)-b Crystalline Porous Aluminophosphate

The porous crystalline aluminophosphate may be one that is comprised of aluminum and phosphorus that are partly substituted by silicon and/or boron, such as a porous crystalline aluminophosphate, silicoaluminophosphate or boroaluminophosphate. The aluminophosphate further may be substituted by other metal atoms or the after-mentioned modified porous crystalline aluminophosphate. The temperature preferably ranges from 30 to 600° C., and the pressure preferably ranges from 20 kPa to 1 MPa The structure of such crystalline porous aluminophosphates may, for example, be those that are identified by codes for zeolites described above as IZA, AEI, AEL, AFI, AFO, AST, CHA, ERI or FAU. Preferred is CHA.

The above porous crystalline aluminophosphate is preferably a porous crystalline silicoaluminophosphate. Specifically, SAPO18, and the like having an AEI structure, SAPO5, and the like having an AFI structure, SAPO41, and the like having an AFO structure, SAPO11, and the like having an AEL structure, SAPO16, and the like having an AST structure, SAPO34, SAPO44, and the like having a CHA structure, SAPO17, and the like having an ERI structure or SAPO37, and the like having a FAU structure may be mentioned. A preferred zeolite has a CHA structure, and particularly preferred is SAPO34.

Various commercial zeolite products nay be used, or it is possible to use zeolites that have been synthesized by a known method disclosed in e.g. "Verified Synthesis of Zeolitic Materials" ($2^{nd}$ Revised Edition 2001 Elsevier) published by the above IZA.

Modified Solid Acid Catalyst

Among the solid acid catalysts that are employed in the present invention, the above mentioned porous crystalline silicates and the above porous mentioned crystalline aluminophosphates are preferably employed and are modified with metal elements of Groups 1 to 14 of the Periodic Table other than silicon and aluminum.

The metal elements of Groups 1 to 14 of the Periodic Table other than silicon and aluminum that are used for modifying the porous crystalline silicate and the porous crystalline aluminophosphate in the present invention are preferably metal elements of Groups 1 to 4 and Groups 7 to 13. Among the metal elements of Groups 1 to 4, metal elements of Groups 1 to 3 are preferred, and metal elements of Groups 1 and 2 are more preferred. Further, among the metal elements of Groups 7 to 13, metal elements of Group 7 are preferred.

Among the metal elements of Groups 1 to 14 of the Periodic Table, with respect to Groups 1 and 2, metal elements in the third to fifth periods of the Periodic Table are preferred, metal elements in the fourth and fifth periods are more preferred, and metal elements in the fourth period are particularly preferred. Further, with respect to Groups 3 to 14, metal elements in the fourth and fifth periods in the Periodic Table are preferred, and metal elements in the fourth period are more preferred. Suitable examples of the preferred metal elements include Na, K, Rb, Cs, Mg, Ca, Sr, Ba, Sc, Y, lanthanoid elements, Mn and Ni. Among them, metal elements that modify the crystalline porous silicate, metal elements of Groups 1 to 4, specifically, Na, K, Rb, Cs, Mg, Ca, Sr and Ba, are preferred, and Na, K, Mg, Ca, Sr and Ba are particularly preferred. Also, metal that modify the porous crystalline aluminophosphate, metal elements in Groups 7 to 13, specifically Mn and Ni, are preferred, and Mn is most preferred.

Further, a zeolite having a structure represented by the codes above: BEA, ERI, FAU, MFI, MOR, MWW or OFF of the IZA, is preferably one that is modified with a metal element of Group 2 of the Periodic Table.

Modifying Method

In the present invention, the above porous crystalline silicates and the above porous crystalline aluminophosphates may be modified with the above metal elements of Groups 1 to 14 by one of several methods of which method (A) is the production of the porous crystalline silicate or the porous crystalline aluminophosphate in the presence of a compound having one of the above metal elements of Groups 1 to 14 of the Periodic Table in the process for producing the porous crystalline silicate or the porous crystalline aluminophosphate, and method (B) where the porous crystalline silicate or the porous crystalline aluminophosphate is treated with a compound of one above metal elements of Groups 1 to 14 of the Periodic Table. Still another method of preparation is to use methods (A) and (B) in combination.

Suitable compounds of the above mentioned metal elements of Groups 1 to 14 of the Periodic Table include salts, oxides and hydroxides of the metals. Salts of the metals include the nitrates, phosphates and chlorides, or organic salts such as a carboxylate such as an acetate. Carbonates may also be employed.

Examples of techniques for producing the porous crystalline silicates or the porous crystalline aluminophosphates in the presence of a compound of the above metal element of Groups 1 to 14 of the Periodic Table using method (A) are found, for example, in JP-A-59-97523 and JP-A-3-101628. In these method embodiments, the compound of the metal element of Groups 1 to 14 of the Periodic Table is present in the raw materials used for the production of the porous crystalline silicate or the porous crystalline aluminophosphate, whereby the metal element is introduced into the crystal lattice resulting in a porous crystalline silicate that is modified with the metal element which is a so-called crystalline metal silicate such as metal silicate, metalloaluminosilicosilicate, metalloaluminophosphosilicate, metaborosilicate or metalloaluminoborosilicate, or a porous crystalline aluminophosphate similarly modified, a so-called crystalline metalloaluminophosphate such as metalloaluminophosphate, metallosilicoaluminophosphate or metalloboroaluminophosphate.

Examples of techniques for treating the porous crystalline silicates or the porous crystalline aluminophosphates with a compound of the above metal element of Groups 1 to 14 of the Periodic Table according to method (B) include, specifically, the following method (B-1), (B-2) or (B-3).

Method (B-1): The porous crystalline silicate or the porous crystalline aluminophosphate is subjected to ion exchange by means of a solution containing the compound of a metal element of Groups 1 to 14 of the Periodic Table in accordance with a usual method to introduce the metal element into the crystal lattice of the silicate or aluminophosphate, thereby preparing a porous crystalline silicate modified with a metal element, i.e. the above mentioned crystalline metallosilicate, or a porous crystalline aluminophosphate likewise modified, i.e. the above mentioned crystalline metalloaluminophosphate.

Method (B-2): The porous crystalline silicate or the porous crystalline aluminophosphate is surface-treated by, e.g. a dipping method, wherein the compound is dipped into a solution containing the compound of the above metal element of Groups 1 to 14 of the Periodic Table in accordance with a usual method, followed by filtration and separation by, e.g. centrifugal separation, or by an impregnation method wherein the compound is immersed in a solution containing the compound of the metal element, followed by evaporation of the solvent to dryness, thereby obtaining a porous crystalline silicate or porous crystalline aluminophosphate, modified with the metal element of Groups 1 to 14 of the Periodic Table.

In the Methods B-1 and B-2, the solvent employed which dissolves the compound of the above metal element is not particularly limited, but usually, water or an alcohol is employed, and water is preferred. Further, the concentration of the solution is usually at least 0.01 wt % and at most is a saturated solution. In the dipping method, it is necessary to consider the water absorption of the porous crystalline silicate or the porous crystalline aluminophosphate, but it is preferred to employ a solution having a high concentration, whereby the metal element can be efficiently introduced. Further, the treatment is conducted so that the amount of the compound of the metal element of Groups 1 to 14 of the Periodic Table in the modified porous crystalline silicate or porous crystalline aluminophosphate is usually at least 0.001, preferably at least 0.01, more preferably at least 0.1 and usually at most 1,000, preferably at most 100, more preferably at most 10, by weight ratio of the metal compound to the silicate or aluminophosphate.

Method (B-3): The porous crystalline silicate or the porous crystalline aluminophosphate is physically mixed with the compound of the metal element of Groups 1 to 14 of the Periodic Table in accordance with a usual method, whereby it is possible to obtain a porous crystalline silicate or a porous crystalline aluminophosphate, modified with the metal element of Groups 1 to 14 of the Periodic Table.

In an embodiment of the physical mixing technique, an oxide or a carbonate is preferred from the viewpoint of the stability under mixing conditions of the compound of the metal element of Groups 1 to 14 of the Periodic Table. Further, the above porous crystalline silicate or the above porous crystalline aluminophosphate, and the compound of the metal element of Groups 1 to 14 of the Periodic Table, are in the form of particles having a particle size of usually at least 0.01 mm and at most 5 mm. However, in order for the mixing treatment to be conducted efficiently, the smaller the particle size of the compound of the metal element, the better. The mixing ratio of the porous crystalline silicate or porous crystalline aluminophosphate to the compound of the metal element of Groups 1 to 14 of the Periodic Table is usually at least 0.001, preferably at least 0.01, more preferably at least 0.1 and usually at most 100, preferably at most 10, more preferably at most 5, by weight ratio considered as the weight of the metal atoms of the metal element to the porous crystalline silicate or aluminophosphate. Further, the mixing apparatus is not particularly limited, and mixing can be conducted by means of a conventional stirring apparatus. However, from the viewpoint of efficiency, it is preferred to employ an apparatus in which pulverization and mixing can be simultaneously conducted. The mixing time may change depending upon the amount to be treated, but is usually at least 1 second, preferably at least 1 minute and usually at most 10 hours, preferably at most 1 hour, more preferably at most 30 minutes.

Among the above modifying methods, method (A) tends to be a solid acid catalyst that has a high initial performance, specifically a high propylene selectivity, as a catalyst, and method (B) tends to result in a solid acid catalyst that exhibits excellent selectivity and catalyst life.

(ii) Lamellar Zeolite

The lamellar zeolite of the present invention is a zeolite that is in a state where a layer of a lamellar precursor is peeled, as disclosed, for example, in "Science and Engineering of Zeolite" p. 10 (published by Kodansha Ltd., 2000). The lamellar zeolite is an aluminosilicate having an acid strength equal to zeolite. It has a structural regularity having short periodicity but not a long periodicity.

Suitable lamellar zeolites include aluminosilicates, wherein the Si/Al molar ratio is at least 5, preferably at least 7.5, more preferably at least 10 and at most 10,000, preferably at most 5,000, further preferably at most 1,000. The aluminosilicate may be one that has a portion or all of Al substituted by an atom from Groups 2 to 14 of the Periodic Table. The atom for substitution may preferably be B, Ti, V, Fe, Zn, Ga, Ge, Zr or Sn.

The lamellar zeolite usually has a BET specific surface area of at least 300 $m^2/g$, preferably at least 400 $m^2/g$, more preferably at least 500 $m^2/g$ and usually at most 2,000 $m^2/g$, preferably at most 1,800 $m^2/g$, more preferably at most 1,500 $m^2/g$. Further, the proportion of the specific surface area of pores ranging from 1.7 nm to 30 nm in the entire BET specific surface area is usually at least 0.4, preferably at least 0.5, more preferably at least 0.6. In XRD, when measured by Cu Kα lines, the zeolite shows no maximum peak at a spacing d of lattice planes being at least 17 Å and shows a peak at from 3 to 4.5 Å.

The pore volume is usually at least 0.3 cc/g, preferably at least 0.5 cc/g and usually at most 3 cc/g, preferably at most 2 cc/g.

Suitable specific examples of the lamellar zeolite include ITQ-2, YNU-1 and ITQ-6. ITQ-2 is preferred.

Method for Producing Lamellar Zeolite

A common method for preparing a lamellar zeolite is the known method disclosed, for example, in Journal of Catalysis 186, 57-63, (1999) or in J. Am. Chem. Soc. 122, 2804-2809, (2000). The method will be described in detail, but it should be understood that the method for producing a lamellar zeolite for use as the catalyst of the present invention is by no means restricted thereto.

First, a silica source, an alumina source, water and a template, and, if necessary, a mineralizer, are mixed, and the mixture is subjected to hydrothermal synthesis. Suitable sources of silica include water glass, silica sol, fine powder silica or an alkyl silicate such as ethyl silicate. Suitable aluminum sources include inorganic salts such as a nitrates, sulfates or chlorides of aluminum; an organic salt such as an acetate; a hydroxide, an oxide, a pseudoboehmite, an alkoxide and sodium aluminate. Suitable template materials include a quaternary alkylammonium salt, an alkylamine, a diamine, an alcoholamine, an alcohol, an ether, an amide, an alkyl urea and a cyanoalkane. A quaternary alkylammonium salt or an amine is preferred.

As the mineralizer, a hydroxide, a hydrogen carbonate or carbonate of an alkali metal or an alkaline earth metal may, for example, be used.

With respect to the ratio of the silica source to the aluminum source, the ratio $SiO_2/Al_2O_3$ is usually at least 1, preferably at least 5, more preferably at least 10 and usually at most 1,000, preferably at most 500, more preferably at most 300.

The molar ratio of water to the silica source is such that the $H_2O/SiO_2$ ratio is usually at least 1, preferably at least 2, more preferably at least 3 and usually at most 200, preferably at most 150, more preferably at most 120.

The ratio of the mineralizer to the silica source is such that the molar ratio of the metal atoms of the mineralizer to $SiO_2$ is usually at least 0.0001, preferably at least 0.001, more preferably at least 0.01 and usually at most 20, preferably at most 10, more preferably at most 8.

The ratio of the template to the silica source is such that the molar ratio of the template to $SiO_2$ is usually at least 0.01, preferably at least 0.02, more preferably at least 0.05 and usually at most 20, preferably at most 10, more preferably at most 6.

The aqueous mixture thus prepared is heated to a temperature of usually at least 80° C., preferably at least 90° C. and usually at most 260° C., preferably at most 220° C. and is subjected to hydrothermal synthesis with or without stirring under ambient pressure or a higher pressure.

The time required for the hydrothermal synthesis is usually at least one hour, preferably at least 5 hours and usually at most 30 days.

The lamellar precursor thus formed is obtained by separation, e.g. filtration, after the hydrothermal synthesis.

For a high silica content zeolite, an organic substance commonly called a template is used during the hydrothermal synthesis. First a precursor is made containing the template synthesized, and the precursor is fired, whereby interlayer dehydration condensation takes place to form a zeolite. In such a zeolite, one obtainable by the hydrothermal synthesis may be one which is a lamellar precursor. As an index to determine whether or not the product is a lamellar precursor, the state is as made is different from the structure after removal of the template by calcination. This can be ascertained, for example, by XRD analysis.

The lamellar precursor may, for example, be a precursor for a MWW zeolite which becomes e.g. MCM22, SSZ25, ITQ1, ERB1 or PSH3 by calcination, a precursor so-called PREFER which becomes FER by calcination, or a lamellar silicate such as PLS-1, RUB-15 or RUB-18.

In a case where a lamellar zeolite is obtained from the lamellar precursor, usually, the interlayer of such a lamellar precursor is broadened by means of e.g. a surfactant, followed by removal of an organic substance by peeling a layer to obtain a lamellar zeolite.

To broaden the interlayer, the lamellar precursor is treated with an aqueous solution containing a surfactant and a quaternary ammonium salt. Suitable surfactants include a water-soluble long chain organic compound, which is usually employed, and a hydroxide or halide of octyltrimethyl ammonium, dodecyltrimethyl ammonium or cetyltrimethyl ammonium, and as the halide, a chloride or a bromide is preferred.

As the quaternary ammonium cation of the salt, it is possible to employ an alkyl ammonium cation that has an alkyl group of at most 8 carbon atoms, such as tetrapropyl ammonium cation.

The blend ratio of the quaternary ammonium salt to the surfactant is such that the quaternary ammonium salt/surfactant ratio is usually at least 0.1, preferably at least 0.2, more preferably at least 0.3 and usually at most 10, preferably at most 5, more preferably at most 3.

The concentration of the aqueous solution is such that the sum of the number of moles of the surfactant and the number of moles of the quaternary ammonium salt, is usually at least 0.1 mol/l, preferably at least 0.2 mol/l, more preferably at least 0.3 mol/l and usually at most 10 mol/l, preferably at most 5 mol/l, more preferably at most 3 mol/l.

The amount of the aqueous solution is such that the weight proportion of the lamellar precursor to the aqueous solution is usually at least 2, preferably at least 4, more preferably at least 10 and usually at most 200, preferably at most 100, more preferably at most 50.

The treating temperature is usually at least 20° C., preferably at least 40° C., more preferably at least 80° C. and usually at most 120° C., preferably at most 110° C., more preferably at most 100° C. The treating time is usually at least 1 hour, preferably at least 7 hours and usually at most 40 hours, preferably at most 25 hours.

After the treatment, the product is, as it is or after once subjected to filtration and washing with water, formed again into a slurry with water, and then layer peeling is carried out. The layer peeling is usually carried out by a known peeling method such as intensive stirring, ultrasonic treatment or spray drying. In the case of intensive stirring or ultrasonic treatment, the peeling time is usually at least 0.5 hour, preferably at least 1 hour and usually at most 100 hours, preferably at most 20 hours.

After the layer peeling, the lamellar zeolite is separated. The separation may be carried out by filtration or by centrifugal separation. However, in the case where the size of the lamellar zeolite is small, an acid such as hydrochloric acid or sulfuric acid may usually be added for flocculation in order to increase the recovery efficiency. Thus, a lamellar zeolite containing a template is obtained. However, in order to remove the template, drying and calcination are carried out to obtain a lamellar zeolite.

The drying temperature is usually at least 80° C. and at most 150° C., and the drying is carried out for usually at least 10 minutes, preferably at least 30 minutes and usually at most 24 hours, preferably at most 12 hours. The calcining temperature is usually at least 300° C., preferably at least 400° C. and usually at most 800° C., preferably at most 600° C., and the calcination is carried out for usually at least 10 minutes, preferably at least 30 minutes and usually at most 24 hours, preferably at most 12 hours.

Suitable lamellar zeolites, synthesized as described above, include ITQ-2 from a MWW type zeolite precursor or ITQ-6 from YNU-1 or PREFER.

The lamellar zeolite thus produced has a short periodic structural regularity and thus has active sites such as acid sites as zeolites usually do but yet is layered which is unusual for zeolites, thereby having a large outer surface. By virtue of such characteristics, in the present invention, it is advantageous for the formation of dispersions and becomes a catalyst excellent in selectivity and durability.

The catalyst may be used for the reaction as it is, or it may be granulated or molded by means of a binder or a substance inert to the reaction and then is used for the reaction. Suitable binders or substances inert to the reaction include alumina or alumina sol, silica, silica gel, quartz, and a mixtures thereof. Mixing with such a substance is effective for reduction of the cost of the entire catalyst or for a function as a heat sink for assisting heat insulation at the time of regeneration of the catalyst, and it is also effective for high densification of the catalyst and for increasing catalyst strength.

(3) Reaction Conditions in the Present Invention

The reaction mode in the process of the present invention is not particularly limited so long as the feed materials constitute a gas phase in the reaction zone, and a known gas phase reaction process using a fluidized bed reactor, a movable bed reactor or a fixed bed reactor, is employed. Further, the reaction may be carried out as a batch system, a semicontinuous system or a continuous system, but it is preferred to carry it out as a continuous system. Such a method may be a method employing a single reactor or a method employing a plurality of reactors disposed in series or in parallel.

According to the present invention, in a process for producing propylene by contacting ethylene with methanol and/or dimethyl ether, the reaction conditions are adjusted so that the amount of ethylene in a reaction mixture being discharged from the reaction system is reduced as compared with the amount of ethylene being fed to the reaction system, and propylene is obtained in a yield of at least 40 mol % based on the sum of the number of moles of methanol and two times the number of moles of dimethyl ether which are being fed to the reaction system.

As far as reaction conditions are concerned, the pressure and the raw material composition can be suitably adjusted. Further, in the case where the reaction is carried out in a continuous system, the rate for feeding the raw materials, is particularly important.

The reaction pressure is usually less than 2 MPa. The reaction pressure is preferably at most 1 MPa, more preferably at most 0.7 MPa, inclusive of a natural pressure. Further, the lower limit is not particularly limited, but is usually at least 0.1 kPa, preferably at least 7 kPa, more preferably at least 50 kPa.

To accomplish the above objects, the reaction pressure is adjusted to within a range of at least 0.1 kPa and less than 2 MPa. In such instances, when the reaction pressure is increased, ethylene as the reaction raw material or propylene as the desired product, is likely to polymerize with an olefin present in the reaction system, whereby the yield of propylene tends to decrease, and when the reaction pressure is lowered, the reaction rate tends to be slow. Accordingly, the pressure is adjusted taking such tendencies into consideration.

With respect to the raw material composition, the amount of ethylene being fed to the reaction system is an excessive amount relative to the methanol and dimethyl ether being fed to the reaction system, i.e. the amount of ethylene being fed to the reaction system is usually at least 1, preferably at least 1.8, more preferably at least 3, as determined by the mole ratio of ethylene to the sum of the number of moles of methanol and two times the number of moles of dimethyl ether. On the other hand, if the amount ethylene is too greatly in excess, problems arise which include costs, the amount of by-products formed and cumbersomeness of operations, and the like. Accordingly, as the upper limit, the amount of ethylene being fed to the reaction system is usually at most 20, more preferably at most 10, particularly preferably at most 6, as a molar ratio, to the sum of the number of moles of methanol and two times the number of moles of dimethyl ether.

In order to accomplish these objectives, the amount of ethylene fed to the reaction system is adjusted within a range of at least 1 and at most 20 as determined by the mole ratio of ethylene to the sum of the number of moles of methanol and two times the number of moles of dimethyl ether which are being fed to the reaction system. In such a case, when the amount of ethylene is increased, a reaction of ethylene with itself is likely to take place, whereby the amount of by-products tends to increase, and when the amount of ethylene is lowered, the reaction of methanol and/or dimethyl ether itself is likely to take place, whereby ethylene, and the like tend to form. Accordingly, the amount is adjusted taking such tendencies into consideration.

Further, adjustment of the amount of ethylene fed to the reaction system within a range of at least 1 and at most 20 as determined by the mole ratio of ethylene to the sum of the number of moles of methanol and two times the number of moles of dimethyl ether which are fed to the reaction system, does not mean adjustment of only the amount of ethylene. One or both of the amount of ethylene and the amount of methanol and/or dimethyl ether may be adjusted so that consequently, the amount of ethylene fed to the reaction system is adjusted within a range of at least 1 and at most 20 as determined by the mole ratio of ethylene to the sum of the number of moles of methanol and two times the number of moles of dimethyl ether.

A suitable raw material feeding rate to conduct the reaction in a continuous system is the weight hourly space velocity (WHSV) per the weight of a catalytically active component, of the sum of methanol and dimethyl ether calculated as methanol, which are fed to the reaction system. The rate is usually at most about 70 $hr^{-1}$, preferably at most 50 $hr^{-1}$, more preferably at most about 30 $hr^{-1}$, further preferably at most 20 $hr^{-1}$. Here, if the WHSV is too small, the yield of the desired product is likely to decrease because of an increase of by-products, and separation tends to be cumbersome. Accordingly, it is usually at least about 0.01 $hr^{-1}$, preferably at least 0.05 $hr^{-1}$, more preferably at least 0.1 $hr^{-1}$, further preferably at least 0.5 $hr^{-1}$.

In order to accomplish the above objectives, the weight hourly space velocity (WHSV) per the weight of a catalytically active component, of the sum of methanol and dimethyl ether calculated as methanol, which are fed to the reaction system, is adjusted within a range of at least 0.01 $hr^{-1}$ and at most 70 $hr^{-1}$. If the WHSV is small, a sequence of consecutive reactions is likely to take place as mentioned above, whereby by-products tend to increase, and the propylene that is formed tends to be consumed. Accordingly, the WHSV is adjusted taking such tendencies into consideration.

In a case where the reaction is carried out in a batch system or in a semicontinuous system, the reaction time may suitably be set depending upon the desired yield of propylene.

Here, if unreacted methanol and unreacted dimethyl ether are present in a large amount in the component that is discharged from the reaction system, the utilization ratio of methanol and dimethyl ether decreases, and no cost merits are obtained. Not only that, the load in separation from propylene as the desired product and in the process for purification of propylene is large, such being undesirable. Further, this reaction is an exothermic reaction, and if a large amount of methanol reacts all at once, temperature control tends to be difficult because of the heat of reaction generated, Further decreases in the yield of the desired product or shortening of the catalyst life, may result. Accordingly, methanol and dimethyl ether are fed to the reactor preferably in a divided fashion.

The method for feeding methanol and dimethyl ether separately from each other varies depending upon the design of the reaction system as to, e.g. whether or not a single reactor is employed or whether a plurality of reactors are disposed in series or in parallel. For example, one method may require a single reactor having a plurality of methanol and dimethyl ether inlets in order to feed the two materials in divided streams, or a method wherein in each of a plurality of reactors, methanol and dimethyl ether inlets are provided to carry out feeding in divided streams. Here, feeding of the divided streams is preferably carried out in such a manner that upon consumption of at least 90% of the methanol and dimethyl ether previously fed, the additional methanol and dimethyl ether are fed.

The reaction conditions such as the reaction temperature in the process of the present invention may optionally be set in accordance with a known process. If unreacted methanol and unreacted dimethyl ether are present in a large amount in the discharged component from the reaction system, the utilization ratio of methanol and dimethyl ether will decrease, and no cost merit is obtained. Not only that, the load in separation from propylene as the desired product and in the purification process of propylene will increase, such being undesirable. Accordingly, considering these factors, reaction conditions are employed in which methanol and dimethyl ether raw material are completely converted.

The reaction temperature employed depends on the type of the catalyst used, but is usually at least about 200° C., preferably at least about 250° C., more preferably at least about 300° C., and the upper limit is usually at most about 700° C., preferably at most about 600° C., more preferably at most about 500° C. If the reaction temperature is too low, the reaction rate tends to be small, the rate for formation of the desired product tends to be significantly slow, and unreacted raw materials tend to remain in large amounts. On the other hand, if the reaction temperature is too high, the yield of the desired product tends to be low.

It should be noted that as the reaction continues, the catalyst is likely to undergo coking in the reactor, which results in a decrease in reaction activities. In such a case, the catalyst may be withdrawn from the reactor, and all or a part of the coke is removed, for example, by oxidizing the accumulated coke in an oxygen-containing atmosphere, thereby regenerating the catalyst. Such a regenerated catalyst may be reintroduced into the reactor. From the viewpoint of such withdrawal and reintroduction of the catalyst, it is preferred to employ a process that uses a movable bed reactor or a fluidized bed reactor rather than a fixed bed reactor, since the operation is thereby simplified.

In the process of the present invention, water is formed as a by-product in the reaction system as the reaction proceeds. However, water is preferably supplied to the reaction system by a method such as adding water to the reaction raw material to let water, i.e. steam, coexist in the reaction system from the initial stage of the reaction. By adding water to the system, the water will function by suppressing the formation of coke which causes deactivation of the catalyst, and it is therefore possible to prolong the life of the catalyst and to suppress formation of paraffins or oligomerization of the olefin which forms, thereby increasing the selectivity of the desired propylene. The amount of water supplied to the reaction system depends on the type of solid acid catalyst used or other reaction conditions, but is usually at least 0.025, preferably at least 0.1, more preferably at least 0.5, as determined by the mole ratio of water to the sum of the number of moles of methanol and two times the number of moles of dimethyl ether which are supplied to the reaction system. If the amount of water supplied is too much, the reaction rate will decrease. This may result in a decrease in the yield of the desired product or the catalyst itself will react with water and undergo modification. Accordingly, the mole ratio of water to catalyst is usually at most 15, preferably at most 10, more preferably at most 5.

The reaction product mixture obtained by the above reaction is one that contains propylene as the main component and ethylene as unreacted raw material. Olefins having at least 4 carbon atoms are also present. The amount of by-products such as the above paraffins, olefins and aromatic hydrocarbons is such that the molar concentration in the hydrocarbon component at the outlet of the reactor is at most 30%, preferably at most 15%. Further, the hydrocarbon component contains ethylene in an amount that is smaller than the amount of ethylene that is fed to the reaction system and contains propylene in an amount of at least 40 mol %, preferably at least 50 mol %, based on the sum of the number of moles of methanol and two times the number of moles of dimethyl ether which are fed to the reaction system.

(4) Method for Separating the Product

In the case where the desired propylene is to be isolated from the above reaction product mixture, the mixture may be introduced into a known separation/purification facility as in an ethylene cracker process, whereby depending upon the respective components, recovery, purification, recycling or a discharge treatment is applied.

In the present invention, the reaction product that results from the reaction of ethylene with methanol and/or dimethyl ether contains olefins having at least 4 carbon atoms that are formed as by-products in addition to the propylene and unreacted ethylene, methanol and dimethyl ether, and further contains a carrier such as ethane, or the like. For purification of propylene the propylene production facility should comprise as components a methane-removing column, an ethane-removing column, a propane-removing column, or the like. However, by recycling the reaction product to the above mentioned facility for the production of lower olefins by thermal decomposition of naphtha, to the facility for the production of lower olefins from methanol and/or dimethyl ether, or to the separation/purification system in the facility for the production of ethylene by steam cracking of ethane, a part of the equipment which should basically be provided for the propylene production facility may be omitted, and the facilities can be minimized.

For example, in the case where propylene is produced by reacting ethylene, which is obtained from an olefin production facility in which naphtha is thermally decomposed, with a gas containing methanol and/or dimethyl ether, it is preferred to introduce the reaction product into the methane-removing column and/or the ethane-removing column and/or the propane-removing column in the facility. It is thereby possible to substantially change the yield balance of ethylene and propylene to increase the propylene/ethylene amount ratio in the production of olefins by thermal decomposition of naphtha, and it is also possible to improve the efficiency in the operation of the facility for the production of olefins by the thermal decomposition of naphtha and at the same time to minimize the facility for the production of propylene from ethylene.

The reaction product contains olefins having at least four carbon atoms that are formed as by-products in addition to the propylene product and unreacted ethylene. Further, in the case where the top fraction in the above front end methane-removing process and the above mentioned front end propane-removing process is used as the ethylene raw material, ethane will also be present, or in the case where the top fraction in the above front end ethane-removing process is used as the ethylene raw material, ethane, methane and hydrogen may, for example, be present. Accordingly, in the purification of propylene, the propylene production facilities for the process of the present invention are preferably provided with a methane-removing column, an ethane-removing column, a propane-removing column, and the like, but depending upon the operational state of the facility for the production of olefins, at least a part of the reaction product may be introduced to the methane-removing column and/or the ethane-removing column and/or the propane-removing column in that facility, whereby it is possible to improve the efficiency in the operation of the facility for the production of olefins by thermal decomposition of naphtha and at the same time to minimize the amount of equipment in the facility for the production of propylene and/or to minimize the capacity of the equipment installed.

In the case where a methane-removing column and/or an ethane-removing column and/or a propane-removing column are installed in the facility for the production of propylene, depending upon the operational states of the facility for the production of olefins and the facility for the production of propylene, it is possible to introduce the product from the facility for the production of olefins to the methane-removing column and/or the ethane-removing column and/or the propane-removing column of the facility for the production of propylene, whereby the allowable range of the facility for the production of olefins can be broadened, and the operational conditions can be optionally changed to maximize the efficiency of the overall process including the facility for the production of olefins and the facility for the production of propylene.

In the case where ethylene is obtained from the facility for the production of lower olefins is employed, it is preferred to recycle the obtained reaction product composed mainly of propylene to a separation/purification system of the facility for the production of lower olefins. In such a case, the separation/purification system of the facility for the production of lower olefins to which the reaction product is to be recycled, may, for example, be a cleaning column or piping thereto, or the ethylene/ethane-removing column or piping thereto. Here, the ethylene-containing fraction is preferably recycled as the raw material for the reaction. Further, in the above reaction, water is also formed as a by-product. Accordingly, a portion of the water that is formed in the reaction system is preferably added to the raw material and recycled to the reaction system.

EXAMPLES

Specific embodiments of the present invention will be shown in the following Examples. However, it should be understood that the present invention is by no means restricted to such Examples.

Example 1-1

An atmospheric pressure fixed bed flow reaction apparatus was employed. A mixture comprising 0.1 g of a catalyst and 0.5 g of a diluent quartz sand was packed in a reaction tube made of PYREX (registered trademark) and having an outer diameter of 6 mm. As the catalyst, SAPO34 prepared in accordance with U.S. Pat. No. 4,440,871 was used, and the reaction was conducted under the following reaction conditions. In Table 1, the reaction results are shown, and gas chromatography was used for the analysis of the product. The methanol conversion, the hydrocarbon composition and the propylene yield represent the values obtained after 70 minutes of reaction time under the reaction conditions stated below.

Reaction Conditions
  Reaction temperature: 400° C.
  Methanol: 6.5 mol %
  Ethylene/methanol (molar ratio)=5
  Water/methanol (molar ratio)=4
  Methanol WHSV=0.5 hr$^{-1}$ Example 1-2

The reaction was conducted in the same manner as described in Example 1-1 except that ZSM5 (SiO$_2$/Al$_2$O$_3$=300) prepared in accordance with the method disclosed in the journal of Institute of Petroleum, 24, (5), 275-280 (1981), was used as the catalyst.

Comparative Example 1

The reaction was conducted in the same manner as in Example 1-1 except that SAPO-34 was used as the catalyst, and the ethylene/methanol (mole ratio) was changed to 0.5.

TABLE 1

|  | Ex. 1-1 | Ex. 1-2 | Comp. Ex. |
|---|---|---|---|
| Catalyst | SAPO-34 | ZSM-5 | SAPO-34 |
| ETY/MeOH (molar ratio) | 5 | 5 | 0.5 |
| H$_2$O/MeOH (molar ratio) | 4 | 4 | 4 |
| MeOH conversion (%) | 100 | 100 | 100 |
| Hydrocarbon composition in the discharged component from the reactor (%) |  |  |  |
| Ethylene | 61.1 | 60.1 | 73.3 |
| Propylene | 28.2 | 14.2 | 18.2 |
| Butene | 3.0 | 10.8 | 5.1 |
| Propylene yield (mol %) based on MeOH fed | 120.4 | 56.6 | 15.7 |

(ETY = ethylene, MeOH = methanol)

Examples 2 to 16

Preparation of Solid Acid Catalyst

Preparation Example 1

Porous crystalline aluminosilicate H-type ZSM5 (SiO$_2$/Al$_2$O$_3$=300) having a MFI structure was obtained in accordance with the method disclosed in the Journal of the Institute of Petroleum, 24, (5), 275-280 (1981). The composition of the porous crystalline aluminosilicate was analyzed by X-ray fluorescence analysis, and the results are shown in Table 2.

Preparation Example 2

A 1 g amount of the porous crystalline aluminosilicate obtained in Preparation Example 1 was mixed with 0.36 g of calcium carbonate obtained by decomposing calcium acetate at 500° C. for 10 hours and then at 550° C. for 6 hours, in a mortar in a solid state, to obtain a porous calcium-mixed crystalline aluminosilicate.

Preparation Example 3

A 1 g amount of the porous crystalline aluminosilicate obtained in Preparation Example 1 was mixed with 0.36 of strontium carbonate obtained by decomposing strontium acetate at 500° C. for 18 hours, in a mortar in a solid state, to obtain a porous strontium-mixed crystalline aluminosilicate.

Preparation Example 4

A porous crystalline porous aluminosilicate H-type ZSM5 (SiO$_2$/Al$_2$O$_3$=50) having a MFI structure was obtained in accordance with the method disclosed in the Journal of the Institute of Petroleum, 24, (5), 275-280 (1981). A 2 g amount of this porous crystalline aluminosilicate was mixed with an aqueous solution having 1.23 g of calcium acetate monohydrate dissolved in 20 ml of water, and the mixture was stirred at about 80° C. for about 20 hours and then evaporated to dryness at a temperature ranging from 100 to 120° C., followed by calcination at 200° C. for two hours and then at 500° C. for 18 hours in air, to obtain a porous calcium-supported crystalline aluminosilicate. The composition of this aluminosilicate was analyzed by X-ray fluorescence, and the results are shown in Table 2.

Preparation Example 5

A porous crystalline aluminoborosilicate as a zeolite having a MFI structure was obtained in accordance with the method disclosed in the Journal of the Institute of Petroleum, 24, (5), 275-280 (1981) using boric acid as a raw material. The composition of this porous crystalline aluminoborosilicate was analyzed by chemical analysis and X-ray fluorescence analysis, and the results are shown in Table 2. A 1 g of this porous crystalline aluminoborosilicate was mixed with an aqueous solution having 0.4 g of calcium acetate monohydrate dissolved in 10 ml of water, and the mixture was stirred at about 80° C. for about 20 hours and then evaporated to dryness at from 100 to 120° C., followed by calcination at 200° C. for two hours and then at 500° C. for 18 hours in air, to obtain a porous calcium-supported crystalline aluminoborosilicate.

Preparation Example 6

A 20 g amount of colloidal silica containing 30 wt % of silica (manufactured by Catalysts & Chemicals Industries Co., Ltd.) and 14 g of water were added to an aqueous solution containing 0.38 g of aluminum nitrate nonahydrate and 0.45 g of calcium acetate monohydrate dissolved in 30 g of water, with stirring. An aqueous solution having 0.42 g of sodium hydroxide dissolved in 6.67 g of water, was added thereto. Further, an aqueous solution having 2.7 g of tetra-n-butylammonium bromide dissolved in 10 g of water, was added, and the mixture was vigorously stirred for two hours. The molar ratios of the SiO$_2$/Al$_2$O$_3$ and CaO/SiO$_2$ charge at that time were 200 and 0.025, respectively. This gel mixture was charged into an autoclave having an internal capacity of 100 ml and subjected to hydrothermal treatment at 180° C. for 48 hours under ambient pressure. The product was collected by filtration, washed with water, dried at 120° C. overnight and calcined at 550° C. for 6 hours in air. 1 g of the product was mixed with 15 ml of 0.8 N hydrochloric acid, subjected to stirring treatment at room temperature for 24 hours, then thoroughly washed with water, then dried at 120° C. overnight and calcined at 550° C. for 6 hours in air, to obtain a H-type porous calcium-containing crystalline aluminosilicate. The composition of this porous calcium-containing crystalline aluminosilicate was analyzed by X-ray fluorescence, and the results are shown in Table 2. This porous calcium-containing crystalline aluminosilicate was mixed with 0.36 g of calcium carbonate obtained by decomposing calcium acetate at 500° C. for 10 hours and then at 550° C. for 6 hours, in a mortar in a solid state, to obtain a calcium-mixed H-type porous calcium-containing crystalline aluminosilicate.

Preparation Example 7

A 1 g amount of the porous calcium-containing crystalline aluminosilicate obtained in Preparation Example 6 was mixed with 0.36 g of strontium carbonate that was obtained by decomposing strontium acetate at 500° C. for 18 hours, in a mortar in a solid state, to obtain a strontium-mixed H-type porous calcium-containing crystalline aluminosilicate.

Preparation Example 8

An aqueous solution containing 20 g of colloidal silica comprising 30 wt % of silica (manufactured by Catalysts & Chemicals Industries Co., Ltd.) and 14 g of water and in addition 0.42 g of sodium hydroxide dissolved in 6.67 g of water were added with stirring to an aqueous solution containing 0.38 g of aluminum nitrate nonahydrate and 0.45 g of magnesium acetate tetrahydrate dissolved in 30 g of water. Further, an aqueous solution containing 2.7 g of tetra-n-butylammonium bromide dissolved in 10 g of water, was added, and the mixture was vigorously stirred for two hours. The molar ratios of $SiO_2/Al_2O_3$ and $CaO/SiO_2$ of the charge were 200 and 0.025, respectively. This gel mixture was charged into an autoclave having an internal capacity of 100 ml and subjected to hydrothermal treatment at 180° C. for 48 hours under ambient pressure. The product was collected by filtration, washed with water, dried at 120° C. overnight and calcined at 550° C. for 6 hours in air. A 1 g amount of the product was mixed with 15 ml of 0.8 N hydrochloric acid, subjected to stirring treatment at room temperature for 24 hours and then thoroughly washed with water, then dried at 120° C. overnight and calcined at 550° C. for 6 hours in air, to obtain a H-type porous magnesium-containing crystalline aluminosilicate. The composition of this porous magnesium-containing crystalline aluminosilicate was analyzed by X-ray fluorescence, and the results are shown in Table 2.

Preparation Example 9

A 1 g amount of the porous magnesium-containing crystalline aluminosilicate obtained in Preparation Example 8 was mixed with 0.36 g of calcium carbonate obtained by decomposing calcium acetate at 500° C. for 10 hours and then at 550° C. for 6 hours, in a mortar in a solid state, to obtain a porous calcium-mixed H-type magnesium-containing crystalline aluminosilicate.

Preparation Example 10

A 1 g amount of the porous magnesium-containing crystalline aluminosilicate obtained in Preparation Example 8 was mixed with 0.36 g of magnesium oxide obtained by decomposing magnesium acetate at 500° C. for 18 hours, in a mortar in a solid state, to obtain a porous magnesium-mixed H-type magnesium-containing crystalline aluminosilicate.

Preparation Example 11

A 1 g amount of the porous magnesium-containing crystalline aluminosilicate obtained in Preparation Example 8 was mixed with 0.36 g of manganese oxide ($Mn_2O_3$) obtained by decomposing manganese oxalate at 500° C. for 18 hours, in a mortar in a solid state, to obtain a manganese-mixed H-type magnesium-containing crystalline porous aluminosilicate.

Preparation Example 12

A 20 g amount of colloidal silica containing 30 wt % of silica (manufactured by Catalysts & Chemicals Industries Co., Ltd.) and 14 g of water and an aqueous solution containing 0.42 g of sodium hydroxide dissolved in 6.67 g of water, were added with stirring to an aqueous solution containing 0.38 g of aluminum nitrate nonahydrate and 0.65 g of barium acetate monohydrate dissolved in 30 g of water. Further, an aqueous solution containing 2.7 g of tetra-n-butylammonium bromide dissolved in 10 g of water was added to the mixed solution, and the mixture was vigorously stirred for two hours. The molar ratios of the $SiO_2/Al_2O_3$ and $BaO/SiO_2$ charge were 200 and 0.025, respectively at that time. This gel mixture was charged into an autoclave having an internal capacity of 100 ml and subjected to hydrothermal treatment at 180° C. for 48 hours under ambient pressure. The product was collected by filtration, washed with water, dried at 120° C. overnight and calcined at 550° C. for 6 hours in air. A 1 g amount of the product was mixed with 15 ml of 0.8 N hydrochloric acid, subjected to stirring at room temperature for 24 hours, then thoroughly washed with water, dried at 120° C. overnight and calcined at 550° C. for 6 hours in air, to obtain a H-type porous barium-containing crystalline aluminosilicate. The composition of this porous barium-containing crystalline aluminosilicate was analyzed by X-ray fluorescence, and the results are shown in Table 2. A 1 g amount of this porous barium-containing crystalline aluminosilicate was mixed with 0.36 g of calcium carbonate obtained by decomposing calcium-acetate at 500° C. for 10 hours and then at 550° C. for 6 hours, in a mortar in a solid state, to obtain a porous calcium-mixed H-type barium-containing crystalline aluminosilicate.

Preparation Example 13

A 15 g amount of colloidal silica containing 30 wt % of silica (manufactured by Catalysts & Chemicals Industries Co., Ltd.) and an aqueous solution containing 0.4 g of sodium hydroxide dissolved in 7.5 g of water were added with stirring, to an aqueous solution containing 0.09 g of aluminum phosphate and 0.34 g of calcium acetate monohydrate dissolved in 25 g of water. Further, an aqueous solution containing 1.96 g of tetra-n-butylammonium bromide dissolved in 10 g of water, was added, and the mixture was vigorously stirred for two hours. The molar ratios of the $SiO_2/Al_2O_3$, $MgO/SiO_2$ and $SiO_2/P_2O_5$ charge at that time were 200, 0.025 and 200, respectively. This gel mixture was charged into an autoclave having an internal capacity of 100 ml and subjected to hydrothermal treatment at 180° C. for 48 hours under ambient pressure. The product was collected by filtration, washed with water, dried at 120° C. overnight and calcined at 550° C. for 6 hours in air. A 1 g amount of the product was mixed with 15 ml of 0.8 N hydrochloric acid, subjected to stirring at room temperature for 24 hours, then thoroughly washed with water, then dried at 120° C. overnight and calcined at 550° C. for 6 hours in air to yield a H-type porous calcium-containing crystalline aluminophosphosilicate. The composition of this porous calcium-containing crystalline aluminophosphosilicate was analyzed by X-ray fluorescence, and the results are shown in Table 2. A 1 g amount of this porous calcium-containing crystalline aluminophosphosilicate was mixed with 0.36 g of calcium carbonate obtained by decomposing calcium-acetate at 500° C. for 10 hours and then at 550° C. for 6 hours, in a mortar in a solid state, to obtain a porous calcium-mixed H-type calcium-containing crystalline aluminophosphosilicate.

Preparation Example 14

A 26.6 g amount of tetra-n-propylammonium bromide (TPABr), 12.4 g of boric acid and 4.8 g of sodium hydroxide were sequentially dissolved in 280 g of water, and then, a mixed liquid comprising 75 g of colloidal silica (SN-40, manufactured by Nissan Chemical Industries, Ltd.) and 35 g of water, was slowly added thereto, followed by stirring thoroughly to yield an aqueous gel. The molar ratio of the $SiO_2/B_2O_3$ charge at that time was 5.0. Then, this gel was charged into an autoclave having an internal capacity of 1,000 ml and subjected to hydrothermal treatment under ambient pressure at 170° C. for 72 hours with stirring at 300 rpm. The product was subjected to pressure filtration, whereby the solid component was separated, thoroughly washed with water and then dried at 100° C. for 24 hours. The catalyst after drying was subjected to calcination at 550° C. for 6 hours in an air stream to obtain a Na-type boroaluminosilicate. A 2.0 g amount of this Na-type boroaluminosilicate was suspended in 40 cc of a 1 M ammonium nitrate aqueous solution and stirred at 80° C. for two hours. The liquid after the treatment was subjected to filtration under reduced pressure, whereby a solid component was separated, thoroughly washed with water and then suspended again in 40 cc of a 1 M ammonium nitrate aqueous solution, followed by stirring at 80° C. for two hours. The liquid after the treatment was filtered under reduced pressure, whereby a solid component was separated, thoroughly washed with water and then dried at 100° C. for 24 hours. The catalyst after the drying was calcined at 500° C. for 4 hours in an air stream to yield a H-type boroaluminosilicate. The composition of the catalyst was obtained by a chemical analysis, and the results are shown in Table 2. Further, by XRD, the structure of zeolite was confirmed to be MFI type.

Preparation Example 15

A 26.6 g amount of tetra-n-propylammonium bromide (TPABr) and 4.8 g of sodium-hydroxide were sequentially dissolved in 280 g of water, and then, a mixed liquid comprising 75 g of colloidal silica (SN-40, manufactured by Nissan Chemical Industries, Ltd.) was slowly added, followed by stirring thoroughly to yield an aqueous gel. Then, this gel was charged into an autoclave having an internal capacity of 1,000 ml and subjected to hydrothermal treatment under ambient pressure at 170° C. for 72 hours with stirring at 300 rpm. The product was subjected to pressure filtration whereby a solid component was separated, thoroughly washed with water and then dried at 100° C. for 24 hours. The catalyst after the drying was calcined at 550° C. for 6 hours in an air stream to yield a Na-type aluminosilicate. A 2.0 g amount of this Na-type aluminosilicate was suspended in 40 cc of a 1 M ammonium nitrate aqueous solution and stirred at 80° C. for two hours. The liquid after the treatment was subjected to filtration under reduced pressure, whereby a solid component was separated, thoroughly washed with water and then suspended again into 40 cc of a 1 M ammonium nitrate aqueous solution, followed by stirring at 80° C. for two hours. The liquid after the treatment was filtered under reduced pressure, whereby a solid component was separated, thoroughly washed with water and then dried at 100° C. for 24 hours. The catalyst after the drying was calcined at 500° C. for 4 hours in an air stream to yield a H-type aluminosilicate. The composition of the catalyst was obtained by a chemical analysis, and the results are shown in Table 2. Further, by XRD, the structure of zeolite was confirmed to be of the MFI type.

TABLE 2

| | $SiO_2/Al_2O_3$ (molar ratio) | MO (wt %) | $MO/SiO_2$ (molar ratio) | $B_2O_3$ (wt %) | $SiO_2/B_2O_3$ (molar ratio) | $P_2O_5$ (wt %) | $SiO_2/P_2O_5$ (molar ratio) |
|---|---|---|---|---|---|---|---|
| Preparation Example 1 | 323 | — | — | — | — | — | — |
| Preparation Example 4 | 53 | 14.0 | 0.27 | — | — | — | — |
| Preparation Example 5 | 110 | — | — | 0.88 | 129 | — | — |
| Preparation Example 6 | 382 | 0.4 | 0.004 | — | — | — | — |
| Preparation Example 8 | 285 | 0.1 | 0.002 | — | — | — | — |
| Preparation Example 12 | 271 | 1.2 | 0.015 | — | — | — | — |
| Preparation Example 13 | 527 | 0.4 | 0.004 | — | — | 0.07 | 3040 |
| Preparation Example 14 | 727 | — | — | 0.68 | 97 | — | — |
| Preparation Example 15 | 711 | — | — | — | — | — | — |

M: Metal

Reaction

For the reaction, an atmospheric pressure fixed bed flow reaction apparatus was used, and a mixture comprising 0.1 g of the porous crystalline aluminosilicate obtained in Preparation Example 1 (Example 2), or 0.136 g of the porous crystalline aluminosilicate or porous crystalline aluminoborosilicate modified with metal elements, obtained in one of Preparation Examples 2 to 13 (Examples 3 to 14), as a solid acid catalyst, and 0.5 g of quartz sand as a diluent, was packed into a reaction tube made of PYREX (registered trademark) and having an outer diameter of 6 mm. A reaction was conducted under the reaction conditions shown in Table 3. The reaction results were analyzed by means of gas chromatography, and the results are shown in Table 3.

TABLE 3

| | | | Reaction conditions | | | | |
|---|---|---|---|---|---|---|---|
| | Catalyst | Methanol (mol %) | Ethylene/ methanol (molar ratio) | Methanol WHSV (hr$^{-1}$) | Water/ methanol (molar ratio) | Reaction temperature (° C.) | Reaction time |
| Ex. 2 | Preparation Example 1 | 6.5 | 5 | 0.5 | 4 | 400 | 40 min 8 hr |
| Ex. 3 | Preparation Example 2 | 6.5 | 5 | 0.4 | 4 | 400 | 40 min 8 hr |
| Ex. 4 | Preparation Example 3 | 6.5 | 5 | 0.4 | 4 | 400 | 40 min 8 hr |
| Ex. 5 | Preparation Example 4 | 6.5 | 5 | 0.1 | 4 | 450 | 40 min 8 hr |
| Ex. 6 | Preparation Example 5 | 6.5 | 5 | 0.1 | 4 | 430 | 40 min 8 hr |
| Ex. 7 | Preparation Example 6 | 6.5 | 5 | 0.4 | 4 | 400 | 40 min 8 hr |
| Ex. 8 | Preparation Example 7 | 6.5 | 5 | 0.4 | 4 | 400 | 40 min 8 hr |
| Ex. 9 | Preparation Example 8 | 6.5 | 5 | 0.5 | 4 | 400 | 40 min 7 hr |
| Ex. 10 | Preparation Example 9 | 6.5 | 5 | 0.4 | 4 | 400 | 40 min 8 hr |
| Ex. 11 | Preparation Example 10 | 6.5 | 5 | 0.4 | 4 | 400 | 40 min 8 hr |
| Ex. 12 | Preparation Example 11 | 6.5 | 5 | 0.4 | 4 | 400 | 40 min 8 hr |
| Ex. 13 | Preparation Example 12 | 6.5 | 5 | 0.4 | 4 | 400 | 40 min 8 hr |
| Ex. 14 | Preparation Example 13 | 6.5 | 5 | 0.4 | 4 | 400 | 40 min 8 hr |
| Ex. 15 | Preparation Example 14 | 6.5 | 5 | 0.25 | 4 | 550 | 40 min 8 hr |
| Ex. 16 | Preparation Example 15 | 6.5 | 5 | 0.25 | 4 | 550 | 40 min 8 hr |

| | Reaction results | | | | |
|---|---|---|---|---|---|
| | Methanol conversion (%) | Hydrocarbon composition in the component discharged from the reactor (mol %) | | | Yield of propylene to methanol fed (mol %) |
| | | Ethylene | Propylene | Butene | |
| Ex. 2 | 100 | 66.3 | 12.8 | 8.7 | 54.8 |
| | 100 | 88.3 | 6.1 | 2.6 | 30.4 |
| Ex. 3 | 100 | 50.2 | 13.7 | 13.4 | 50.8 |
| | 100 | 71.0 | 10.6 | 8.2 | 45.9 |
| Ex. 4 | 100 | 21.2 | 14.6 | 15.9 | 44.3 |
| | 100 | 68.3 | 11.5 | 9.1 | 48.9 |
| Ex. 5 | 100 | 38.1 | 21.2 | 15.3 | 73.5 |
| | 100 | 45.8 | 19.8 | 14.4 | 72.9 |
| Ex. 6 | 100 | 38.5 | 24.0 | 15.8 | 85.7 |
| | 100 | 34.1 | 24.1 | 16.8 | 82.6 |
| Ex. 7 | 100 | 14.1 | 14.6 | 14.3 | 39.5 |
| | 100 | 46.3 | 16.4 | 13.1 | 58.3 |
| Ex. 8 | 100 | 16.6 | 14.5 | 14.8 | 13.7 |
| | 100 | 45.8 | 17.1 | 14.1 | 60.8 |
| Ex. 9 | 100 | 49.8 | 22.3 | 12.1 | 85.0 |
| | 100 | 72.8 | 13.2 | 5.9 | 58.8 |
| Ex. 10 | 100 | 55.3 | 21.1 | 10.4 | 84.0 |
| | 100 | 73.7 | 12.9 | 5.9 | 57.7 |
| Ex. 11 | 100 | 53.4 | 22.4 | 10.6 | 88.2 |
| | 100 | 71.9 | 13.8 | 5.9 | 61.2 |
| Ex. 12 | 100 | 31.9 | 24.7 | 14.3 | 81.6 |
| | 100 | 59.2 | 18.0 | 9.0 | 73.0 |
| Ex. 13 | 100 | 24.0 | 21.2 | 12.6 | 65.3 |
| | 100 | 67.1 | 15.7 | 7.0 | 67.8 |
| Ex. 14 | 100 | 39.6 | 21.3 | 15.0 | 73.8 |
| | 100 | 80.3 | 9.5 | 4.6 | 44.3 |
| Ex. 15 | 100 | 75.5 | 16.0 | 4.9 | 75.2 |
| | 100 | 75.6 | 15.9 | 4.9 | 74.8 |
| Ex. 16 | 100 | 76.0 | 15.7 | 4.6 | 73.8 |
| | 100 | 76.1 | 15.7 | 4.5 | 73.8 |

As is evident from the results shown in Table 3, as compared with the case of Example 2 wherein a non-modified porous crystalline silicate was used as a solid acid catalyst, in the case of Example 3 or 4 wherein a porous crystalline silicate modified with calcium or strontium was used, the yield of propylene to methanol fed shows a high yield even after 8 hours of the reaction time against after 40 minutes of the reaction time, and the difference in yield between the two reaction times is −4.9% or +4.6%, respectively, while in Example 2, the yield is low and decreases by −24.4% between the two reaction times. Namely, it is evident that according to the process of the present invention, a high yield can be accomplished, and at the same time a decrease in yield for an operation for a long time can be suppressed. Further, as shown in Examples 5 to 12, it is evident that also in the case wherein a porous crystalline silicate modified with other metal elements is used as a solid acid catalyst, a high yield can be accomplished, and at the same time, a decrease in yield of propylene over a long operational time period can be suppressed.

Example 17

Preparation Of Catalyst

MCM22 precursor: A 0.8 g amount of 70% NaAlO$_2$ and 1.4 g of NaOH were dissolved and stirred in 162 g of deionized water. When a transparent aqueous solution had formed, 9.9 g of hexamethyleneimine and 12 g of silica (AEROSIL 200, by NIPPON AEROSIL CO., LTD.) were added, followed by stirring for two hours. The obtained slurry was divided into two 100 ml autoclaves and subjected to tumbling at 150° C. for 7 days. The autoclaves were cooled and then, the contents were collected by filtration, washed with water and dried at 120° C. to yield a MCM22 precursor.

ITQ-2: A 4.5 g amount of MCM22 precursor was added to an aqueous solution having 5.1 g of hexadecyltrimethylammonium bromide and 5.5 g of 40% of tetrapropylammonium hydroxide dissolved in 12.4 g of water, followed by refluxing at 80° C. for 16 hours. The obtained slurry was treated for one hour with ultrasonic waves. Then, a 0.25 M hydrochloric acid solution was added dropwise to bring the pH to at most 2, followed by filtration, washing with water, then drying and calcination at 550° C. for 24 hours, to yield a ITQ-2, which was used as a catalyst.

Reaction

A reaction was conducted in the same manner as described in Example 2 except that 0.1 g of ITQ-2 obtained in the above method was used as the catalyst. Gas chromatography was employed for the analysis of the product. The reaction results after 40 minutes and after 8 hours from the initiation of the reaction are shown in Table 4.

TABLE 4

|  | Ex. 17 | | Ex. 2 | |
| --- | --- | --- | --- | --- |
| Catalyst | ITQ-2 | | ZSM-5 | |
| Reaction time (min) | 40 | 480 | 40 | 480 |
| Methanol conversion (%) | 100.0 | 100 | 100 | 100 |
| Hydrocarbon composition in the reaction product (%) Ethylene | 18.6 | 19.3 | 66.3 | 88.3 |
| Propylene | 9.6 | 15 | 12.8 | 6.1 |
| Butene | 9.1 | 15.5 | 8.7 | 2.6 |
| Yield of propylene to methanol fed (%) | 29.3 | 48.7 | 54.8 | 30.4 |
| Change in yield of propylene (%/hr) | 2.7 | | −3.3 | |

As is evident from the results shown in Tale 4, when ITQ-2 being lamellar zeolite, is employed, the change in yield of propylene in the time period of after 40 minutes to after 8 hours of reaction is 2.7, and thus, even in a reaction over a long period of time, both the conversion of methanol as the reaction substrate and the yield of propylene could be maintained at high levels. Whereas, when ZSM-5 is employed, the change in yield of propylene in the time period of after 40 minutes to after 8 hours, is −3.3, and the yield of propylene decreases as the time passes, although after 40 minutes, both the conversion and the yield of propylene show high levels.

Namely, it is evident that in Example 2, because of the decrease in the catalytic activity, it was not possible to use the catalyst for a long period of time, while in Example 15, the yield of propylene does not decrease, and propylene can be obtained constantly.

The entire disclosures of Japanese Patent Application No. 2003-415367 filed on Dec. 12, 2003, Japanese Patent Application No. 2004-45917 filed on Feb. 23, 2004, Japanese Patent Application No. 2004-45918 filed on Feb. 23, 2004, Japanese Patent Application No. 2004-45919 filed on Feb. 23, 2004, Japanese Patent Application No. 2004-101075 filed on Mar. 30, 2004, Japanese Patent Application No. 2004-134145 filed on Apr. 28, 2004 and Japanese Patent Application No. 2004-153547 filed on May 24, 2004 including specifications, claims and summaries are incorporated herein by reference.

What is claimed is:

1. A process for producing propylene, which comprises:
    mixing ethylene and methanol and/or dimethyl ether in a mole ratio range of at least 1 to at most 20 moles ethylene to the sum of the number of moles of methanol and two times the number of moles of dimethyl ether; and
    reacting ethylene and methanol and/or dimethyl ether of the mixture in the presence of a catalyst, wherein
    the amount of ethylene that is discharged from the reaction system is controlled to a reduced level in comparison to the amount of ethylene that is fed into the reaction system, and
    the yield of propylene is controlled to at least 40 mol %, based on the sum of the number of moles of methanol and two times the number of moles of dimethyl ether, which are fed into the reaction system.

2. The process for producing propylene according to claim 1, wherein
    the reaction is conducted under a pressure that is adjusted within the range of at least 0.1 kPa to less than 2 MPa.

3. The process for producing propylene according to claim 1, wherein
    a weight hourly space velocity per weight of a catalytically active component, of the sum of methanol and dimethyl ether calculated as methanol, which are fed to the reaction system, is adjusted within the range of at least 0.01 hr$^{-1}$ and at most 70 hr$^{-1}$.

4. The process for producing propylene according to claim 1, wherein the mole ratio of the amount of ethylene fed to the reaction system to the sum of the number of moles of methanol and two times the number of moles of dimethyl ether which are fed to the reaction system is at least 1.8.

5. The process for producing propylene according to claim 1, wherein the catalyst is a solid acid catalyst.

6. The process for producing propylene according to claim 5, wherein the solid acid catalyst is a zeolite.

7. The process for producing propylene according to claim 6, wherein the zeolite is a porous crystallizable silicate modified with a metal element of Groups 1 to 14 of the Periodic Table other than silicon and aluminum, or a porous crystallizable aluminophosphate likewise modified.

8. The process for producing propylene according to claim 5, wherein the solid acid catalyst is a lamellar zeolite.

9. The process for producing propylene according to claim 1, wherein water is fed into the reaction system.

10. The process for producing propylene according to claim 1, wherein the ethylene is obtained from a facility for the production of olefins by thermal decomposition of naphtha.

11. The process for producing propylene according to claim 1, wherein the ethylene is obtained from a facility for the production of lower olefins using methanol and/or dimethyl ether as raw materials.

12. The process for producing propylene according to claim 1, wherein the ethylene is obtained from a facility for the production of ethylene by steam cracking of ethane.

13. The process for producing propylene according to claim 1, wherein the reaction of ethylene with methanol and/or dimethyl ether is conducted under a pressure ranging from at least 0.1 kPa to at most 1 MPa.

14. The process for producing propylene according to claim 1, wherein ethylene is fed to the reaction system in a molar amount of at least 3 mole to at most 6 moles based on the sum of the number of moles of methanol and two times the number of moles of dimethyl ether.

15. The process for producing propylene according to claim 1, wherein a summed amount of methanol and dimethyl ether calculated as methanol are fed into a reactor at a weight hourly space velocity ranging from 0.01 $hr^{-1}$ to at most 70 $hr^{-1}$.

16. The process for producing propylene according to claim 15, wherein said weight hourly space velocity ranges from 0.05 $hr^{-1}$ to at most 50 $hr^{-1}$.

17. The process for producing propylene according to claim 1, wherein the reaction is conducted at a temperature ranging from 200 to 700° C.

18. The process for producing propylene according to claim 17, wherein said reaction temperature ranges from 250 to 600° C.

19. The process for producing propylene according to claim 1, wherein the reaction is conducted in the presence of a supply of water ranging from at least 0.025 to at most 15 in terms of a mole ratio of water relative to the sum of the number of moles of methanol and two times the number of moles of dimethyl ether which are being fed to the reaction system.

* * * * *